(12) United States Patent
Ales et al.

(10) Patent No.: US 8,114,030 B2
(45) Date of Patent: Feb. 14, 2012

(54) BREASTFEEDING QUANTIFICATION

(75) Inventors: Thomas Michael Ales, Neenah, WI (US); Rick D. Mosbacher, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 287 days.

(21) Appl. No.: 11/846,840

(22) Filed: Aug. 29, 2007

(65) Prior Publication Data

US 2008/0077040 A1 Mar. 27, 2008

Related U.S. Application Data

(63) Continuation-in-part of application No. 11/511,583, filed on Aug. 29, 2006.

(51) Int. Cl.
 *B65D 81/00* (2006.01)

(52) U.S. Cl. .......................... 600/584; 600/546; 607/40

(58) Field of Classification Search .................. 600/546
 See application file for complete search history.

(56) References Cited

U.S. PATENT DOCUMENTS

| | | | |
|---|---|---|---|
| 4,571,750 A | 2/1986 | Barry | |
| 4,926,871 A | 5/1990 | Ganguly et al. | |
| 5,263,491 A * | 11/1993 | Thornton | 600/587 |
| 5,322,067 A | 6/1994 | Prater et al. | |
| 5,454,376 A | 10/1995 | Stephens et al. | |
| 5,666,104 A | 9/1997 | Pollack et al. | |
| 5,827,191 A | 10/1998 | Rosenfeld | |
| 6,110,111 A | 8/2000 | Barnard | |
| 6,359,190 B1 | 3/2002 | Ter Ovanesyan et al. | |
| 6,484,053 B2 | 11/2002 | Leelamanit et al. | |
| 6,667,725 B1 | 12/2003 | Simons et al. | |
| 6,970,091 B2 | 11/2005 | Roe | |
| 7,330,753 B2 | 2/2008 | Policker et al. | |
| 2003/0208113 A1 | 11/2003 | Mault et al. | |
| 2004/0147816 A1 * | 7/2004 | Policker et al. | 600/300 |
| 2005/0146988 A1 | 7/2005 | Dolson | |
| 2005/0177099 A1 | 8/2005 | Dahan et al. | |
| 2005/0251036 A1 | 11/2005 | Abuhamad | |
| 2005/0283327 A1 | 12/2005 | Bowman et al. | |
| 2006/0064037 A1 * | 3/2006 | Shalon et al. | 600/586 |
| 2009/0054771 A1 | 2/2009 | Kolberg et al. | |

FOREIGN PATENT DOCUMENTS

JP 7088112 A 4/1995

(Continued)

OTHER PUBLICATIONS

Barry et al. "Acoustic Myography" 2004, Astro-Med, Inc. pp. 1-4.*

(Continued)

*Primary Examiner* — Max Hindenburg
*Assistant Examiner* — Renee Danega
(74) *Attorney, Agent, or Firm* — Dority & Manning, P.A.

(57) ABSTRACT

Presented is a method for quantifying breastfeeding between a mother and a baby, the method including measuring a physiological volume indicative of stomach fullness volume for the baby; setting a signal threshold value of the physiological volume to correspond to a stomach level that is less than or equal to the stomach fullness volume; obtaining an objective measurement of the physiological volume indicative of a level of fullness of the baby's stomach; and providing an indication to the mother when the objective measurement equals or exceeds the signal threshold value. In one embodiment, for instance, the baby's swallows may be recorded for determining the volume of breast milk consumed by the baby.

22 Claims, 2 Drawing Sheets

FOREIGN PATENT DOCUMENTS

| | | |
|---|---|---|
| WO | WO 0154488 A1 | 8/2001 |
| WO | WO 02082968 A2 | 10/2002 |
| WO | WO 2005016220 A2 | 2/2005 |
| WO | WO 2006035446 A2 | 9/2005 |
| WO | WO 2005/092177 * | 10/2005 |
| WO | WO 2005092177 A1 | 10/2005 |
| WO | WO 2006003655 A1 | 1/2006 |
| WO | WO 2006034394 A1 | 3/2006 |
| WO | WO 2006/035446 * | 4/2006 |
| WO | WO 2006054287 A1 | 5/2006 |

OTHER PUBLICATIONS

Grant, Kerrin. "Hand-Rearing Cheetah Cubs: Milk Formulas 2005" http://www.catsg.org/cheetah/05_library/5_3_publications/G/Grant2005_Hand-rearing_cheetah_cubs_milk_formula.pdf.*

English Abstract of JP0788112A dated Apr. 1995, European Patent Office.

Fisher et al. "Breast-Feeding Through the First Year Predicts Maternal Control in Feeding Subsequent Toddler Energy Intakes," *Journal of the American Dietetic Association*, vol. 100, No. 6, Jun. 2000: 641-646.

Kahrilas et al. "Volume Accommodation During Swallowing," *Dysphagia*, vol. 8, 1993: 259-265.

Meier, Paula P. et al. "Estimating Milk Intake of Hospitalized Preterm Infants Who Breastfeed," *Journal of Human Lactation*, vol. 12, No. 1, Mar. 1996:21-26.

Moreau-Gaudry, Alexandre et al. "Use of Respiratory Inductance Plethysmography for the Detection of Swallowing in the Elderly" *Dysphagia*, vol. 20, No. 4, Fall 2005: 297-302.

Ramsay et al. "Ultrasound Imaging of Milk Ejection in the Breast of Lactating Woman," *Pediatrics*, vol. 113, No. 2, Feb. 2004: 361-367.

Stevens, Susan et al. "How Accurate is Clinical Test Weighing of the Newborn?" *Midwives Chronicle*, vol. 93 (1108), May 1980:148-149.

Acoustic Myography (AMG): A live Demonstration by ® GRASS, Published by Astro-Med, Inc., 2004: 4 pages.

Barry et al. "Acoustic Myography: A Noninvasive Monitor of Motor Unit Fatigue," *Muscle & Nerve*, vol. 8, No. 3, 1985: 189-194.

Buckley et al. "Benefits and Challenges of Transitioning Preterm Infants to At-Breast Feedings," *International Breastfeeding Journal*, vol. 1, No. 13, Published online Aug. 31, 2006: 14 pages.

Butte, N. et al. "The Start Healthy Infant and Toddler Feeding Guidelines," *Nutrition & Your Child*, Children's Nutrition and Research Center, vol. 14, No. 3, Published online Aug. 2004: 1-4.

"High-Risk Newborn," University of Utah Health Sciences Center, Published online Apr. 2003: 10 pages.

Daly, Steven E.J. et al. "The Short-Term Synthesis and Infant-Regulated Removal of Milk in Lactating Women," *Experimental Physiology*, vol. 78, 1993, pp. 209-220.

International Search Report, PCT/IB2008/052514, dated Jan. 30, 2009.

Arthur et al. "Measuring Short-Term Rates of Milk Synthesis in Breast-Feeding Mothers" Quarterly Journal of Experimental Physiology (1989) p. 419-428.

Guardo et al. "Contactless Measurement of Thoracic Conductivity Changes by Magnetics Induction" IEEE/EMBS Nov. 2, 1997 p. 2450-2453.

English Abstract of Japanese Patent No. 7088112A.

PCT/IB2008/052511 International Search Report, Jan. 30, 2009.

* cited by examiner

BREASTFEEDING QUANTIFICATION

RELATED APPLICATIONS

The present application is a continuation-in-part application and claims priority to U.S. patent application Ser. No. 11/511,583, filed on Aug. 29, 2006.

BACKGROUND

This invention relates to a method for reassuring a nursing mother that her baby is receiving sufficient breast milk and therefore sufficient nutrition. The method uses an objective measurement indicative of the amount of breast milk swallowed by the baby.

Mothers of newborn babies have a strong need to understand how much their baby has breast fed. There were 4.1 million births in the United States alone in 2003 and about 70% of all new moms breast feed. The first two weeks of breastfeeding show the largest declines in breastfeeding with 10% drop off each week. There is a significant opportunity to reassure (especially first-time) mothers that their babies are breastfeeding appropriately, particularly during the first weeks when mom is unsure and not confident in her breastfeeding ability. The mother does not know the state of her baby's stomach and may question whether her baby's stomach is sufficiently full.

Prior devices have attempted to quantify breastfeeding by interposing a flow meter between mother and baby. Such devices can lead to obvious problems with delivery, intimacy, and bonding between mother and baby.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention.

SUMMARY

Mothers can be provided with reassurance and a sense of security without adversely affecting the sensory experience and by providing safe, comfortable, easy ways for a mother to care for her baby. Giving a mother a tool to help evaluate whether her baby is getting enough breast milk will help reassure the mother with respect to how well breastfeeding is going and provide her with a sense of security regarding her baby's health. The present invention solves the problems outlined above by providing a method for reassuring a nursing mother that her baby is receiving sufficient breast milk and therefore sufficient nutrition. The method uses an objective measurement indicative of the amount of breast milk swallowed by the baby.

For example, in one aspect of the present invention, the invention includes a method for quantifying breastfeeding between a mother and a baby, the method including measuring a physiological volume indicative of stomach fullness volume for the baby; setting a signal threshold value of the physiological volume to correspond to a stomach level that is less than or equal to the stomach fullness volume; obtaining an objective measurement of the physiological volume indicative of a level of fullness of the baby's stomach; and providing an indication to the mother when the objective measurement equals or exceeds the signal threshold value.

In another aspect of the present invention, the invention includes a method for training a mother to recognize when her breastfeeding baby is receiving adequate nutrition, the method including providing a device adapted to supply a measurement of a physiological trait indicative of stomach fullness volume for the baby over at least one time period during which at least one breastfeeding event occurs; providing instructions to the mother with respect to expected traits exhibited by a baby with a full or mostly full stomach; and demonstrating a correlation between the measurement and the expected traits exhibited by a baby with a full or mostly full stomach.

In another aspect of the present invention, the invention includes a method for training a mother to recognize when her breastfeeding baby is receiving adequate nutrition, the method including setting a signal threshold value of a physiological volume to correspond to a stomach level that is less than or equal to a stomach fullness volume; obtaining an objective measurement of the physiological volume indicative of a level of fullness of the baby's stomach; and providing an indication to the mother when the objective measurement equals or exceeds the signal threshold value.

In another aspect of the present invention, the invention includes a method for quantifying breastfeeding between a mother and a baby, the mother having a breast, the method including measuring a physiological trait indicative of breast fullness volume of the breast; setting a signal threshold value of the physiological trait to correspond to a reduction in breast level that is less than or equal to the breast fullness volume; obtaining an objective measurement of the physiological trait indicative of a reduction in level of fullness of the mother's breast; and providing an indication to the mother when the objective measurement equals or exceeds the signal threshold value.

In another aspect, the present disclosure is directed to a method and system for quantifying the amount of a nourishing composition that is being consumed by a baby. In this embodiment, for instance, the method can include the step of sensing a baby's swallows during consumption of the nourishing composition. A volume of the nourishing composition is then determined based upon the number of swallows sensed.

The above method can be used, for instance, during breastfeeding in order to provide the mother with an objective measurement of the volume of the nourishing composition being consumed by the baby which can correspond to a stomach fullness volume.

In general, any suitable instrument can be used to sense the baby's swallows. For instance, in one embodiment, the baby's swallows can be sensed by sensing muscular impulses in the esophagus of the baby. For instance, the baby's swallows may be sensed using electromyography, such as surface electromyography. Alternatively, the swallows can be sensed using acoustic myography. In still another embodiment, the swallows may be sensed using a microphone or using a strain gauge.

The sensor used to sense the swallows of the baby can be communicated, for instance, to a monitor. The monitor may comprise any suitable programmable device that contains an algorithm for determining the amount of the nourishing composition the baby has consumed based upon the number of swallows. The monitor may include a display for communicating to a user the volume of the nourishing composition the baby has consumed.

BRIEF DESCRIPTION OF THE DRAWINGS

The foregoing and other features and aspects of the present invention and the manner of attaining them will become more apparent, and the invention itself will be better understood by reference to the following description, appended claims and accompanying drawings, where:

Repeat use of reference characters in the present specification and drawings is intended to represent the same or analogous features or elements of the present invention. The drawings are representational and are not necessarily drawn to scale. Certain proportions thereof may be exaggerated, while others may be minimized.

DETAILED DESCRIPTION OF THE INVENTION

It is to be understood by one of ordinary skill in the art that the present discussion is a description of exemplary aspects of the present invention only, and is not intended as limiting the broader aspects of the present invention.

For the purposes of this invention, "mother" is defined as the person who is breastfeeding a baby, whether that person is or is not the actual birth mother. "Mother" may also refer to a caregiver, male or female, who is bottle-feeding or otherwise providing nutrition to a baby. Similarly, the term "baby" may also refer to a subject of any age who is receiving nutrition but cannot communicate stomach fullness in a meaningful manner.

"Physiological trait" is any feature, size, volume, action, characteristic, or quality of part or all of a human body. "Physiological volume" is a subset of physiological trait and refers to the volume of a human organ, where a human organ includes but is not limited to a stomach, a breast, and a bladder. Physiological volume may be measured directly (e.g. by ultrasound) or indirectly (e.g. by measuring the strain in skin near the organ).

The achievement of suitable nutrition levels in a baby can be enhanced by measurement of a full or mostly full stomach and/or recognition by the mother of traits associated with a full or mostly full stomach. The method of this invention involves the identification of appropriate nutritional training opportunities that can aid a mother in recognizing when her breastfeeding baby has a full or mostly full stomach. The term "appropriate" as used herein in relation to a nutritional training opportunity refers to an occurrence or a condition that is especially suitable for use in training the mother to recognize when the baby's stomach contains a sufficient quantity of breast milk. Thus, the nutritional training method of the present invention includes the steps of obtaining an objective measurement of a physiological trait or volume that is indicative of the physical state of the stomach and providing an indication to the mother when the value of the measurement reaches some signal threshold value corresponding to a full or relatively full stomach. The objective measurement is preferably taken concurrent with breastfeeding so that the mother may monitor the progress of the breastfeeding without interrupting the breastfeeding.

The occurrence of this state of fullness of the stomach provides an appropriate opportunity to train the mother to recognize the traits of the baby associated with a full or mostly full stomach. By providing the indication based upon the objective measurement, this method can identify appropriate nutritional training opportunities to the mother. Given this objective indication of relative stomach fullness, the mother may observe the baby's actions, reactions, and demeanor to identify traits associated with stomach fullness, with the goal of eventually recognizing when the baby has a full stomach without an objective measurement. Because this method is based on an objective measurement of a physiological trait or volume and does not require the baby to communicate stomach fullness or the mother to guess when stomach fullness exists, this method of nutritional training is usable with babies far before they are capable of verbal communication.

Preferably, the signal threshold value is set such that it indicates a relatively full stomach. The volume of breast milk in the stomach at which the stomach is considered full is referred to herein as the "stomach fullness volume" of the stomach. The value of the objective measurement corresponding to the amount of breast milk in the stomach is referred to herein as the "physiological trait level" or the "physiological volume level." This physiological trait or volume level may be measured and used to determine the signal threshold value. Because the stomach fullness volume varies somewhat between different breastfeeding events, an average of the stomach fullness volume or of the corresponding physiological trait or volume level may be used to determine the signal threshold value. Alternatively, the lowest or highest observed physiological trait or volume level, another empirically derived value, or even an arbitrary value, may be used to determine the signal threshold value. For example, the signal threshold value may be set to correspond to an average of the daytime breastfeeding volume.

In addition, the invention described herein may be equally applied to bottle-fed babies to determine their stomach fullness volumes and physiological trait or volume levels. Examples of situations in which babies may be bottle-fed include post-breastfeeding, instead of breastfeeding, or in a medical care situation. A mother or caregiver can know the volume of fluid consumed by the baby based on the amount that is removed by the baby from the bottle, but may need additional guidance concerning the baby's fullness. General rules of feeding volumes versus age or feeding to rejection of the bottle provide decent guidelines for the average baby, but a mother or caregiver may desire or require more particular information related to a particular baby.

Various methods may be used to determine the physiological trait or volume level of interest. The amount of breast milk as an input may be inferred from the amount of urinary and fecal output of the baby, such as from a regular or random sampling of the volume of urinary and fecal output retained in a diaper or other article worn by the incontinent baby. Typically, the dry and wet weights of a diaper may be compared to estimate the volume of urine retained in the diaper, which may then be related back to the breast milk intake. Similarly, in accordance with the concept introduced above and applied throughout this description, an indirect parameter, such as the physiological trait or volume level, may be used in lieu of a direct determination of a volume of interest. A monitor or monitors as described herein may be used to determine the stomach volume and physiological trait or volume level of interest. For example, the monitor may be used to track the baby's stomach volume and level, or other objective measurement of a physiological trait or volume indicative of the physical state of the stomach, over one or more time periods during which at least one breastfeeding event occurs. The local maximum of the stomach volume or level or other objective measurement of a physiological trait or volume generally corresponds to the baby's stomach fullness volume.

Ideally, the signal threshold value should be set high enough to correspond to a stomach volume at which the stomach is full or mostly full to ensure the baby receives suitable nutrition and perhaps to maximize the timing between breastfeeding events. In any case, the signal threshold value should be set high enough that the baby is likely to experience the physical sensation of stomach fullness at the time that the signal is provided. Setting the signal threshold value at this level will help to ensure that the opportunity is provided for the baby to act or react as the baby normally would with a full stomach, thus giving the mother the opportunity to observe such actions and reactions. In one aspect of the present invention, the signal threshold value is set to correspond to a specific percentage or proportion of the stomach fullness volume. For example, the signal threshold value is set to correspond to a stomach level that is about 90% or less of the stomach fullness volume. In another example, the signal threshold value is set to correspond to a stomach level that is about 80% or less of the stomach fullness volume. In yet another example, the signal threshold value is set to correspond to a stomach level that is about 70% or less of the stomach fullness volume.

Use of the signal threshold relies on the general relationship between the level of breast milk in the stomach, designated "stomach level," and the magnitude of the corresponding physical sensation, designated "stomach sensation," that is associated with the distending stomach. As an individual's stomach begins to fill, it initially expands with very little increase in internal pressure and with the physical sensation at a level that is too low to be discernible by the individual. As the stomach continues to fill, the internal pressure and the magnitude of the physical sensation increase until the physical sensation eventually becomes discernible by the individual. At this point of potential discernment of the physical sensation, the opportunity is presented for the individual to become aware of the sensation. The "stomach sensation threshold" represents a magnitude of the physical sensation at which a hypothetical, but representative, individual, such as a baby, may become aware of the physical sensation of the fullness of the stomach.

The stomach level at which the stomach sensation reaches the stomach sensation threshold is designated the "threshold stomach level" for the individual. The threshold stomach level is generally less than the stomach level at which stomach fullness typically occurs for the individual. Also, the onset of discernible sensation may be gradual over a range of stomach levels. In the case of such a gradual onset, the stomach sensation threshold may correspond to a range of stomach levels rather than to a discrete value. The stomach sensation threshold, and therefore the threshold stomach level, may change over time as the individual grows.

Figure 1:
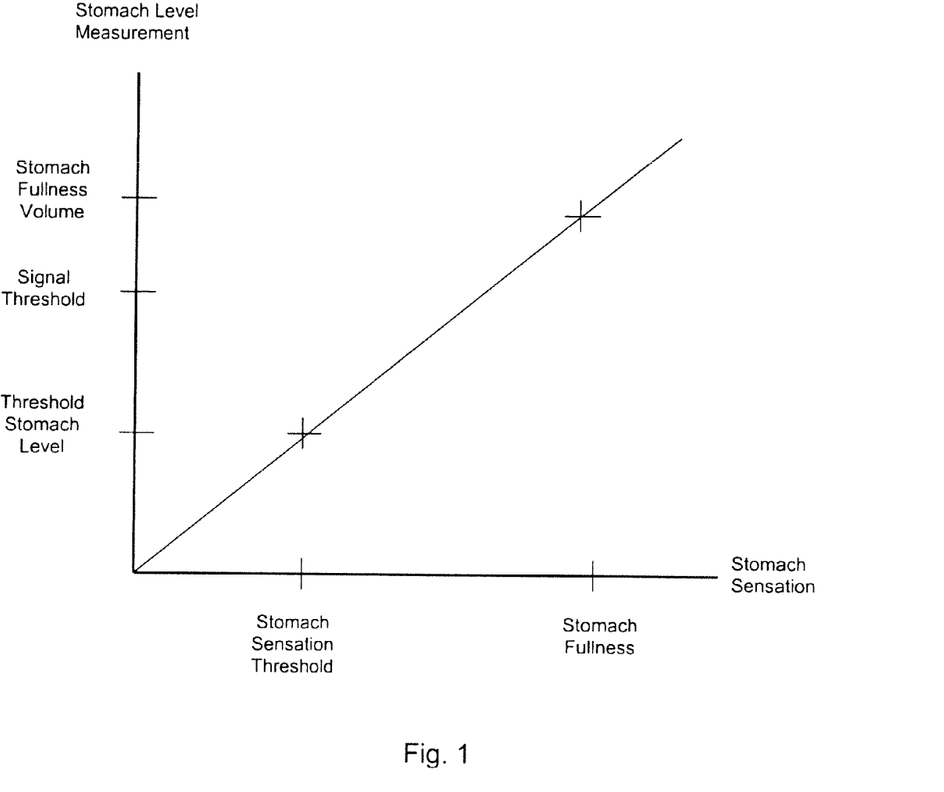
FIG. 1 shows the general relationship between a representative objective measurement that is indicative of the physical state of the stomach and the volume of the stomach.

FIG. 1 depicts an example of a representative objective measurement that is indicative of the physical state of the stomach, as a function of the stomach level. To facilitate the effective association between discernible, or potentially discernible, stomach sensation and the physical possibility of stomach fullness, an indication is provided at a stomach level that is greater than the threshold stomach level, but less than the stomach fullness volume. Accordingly, the signal threshold is set at a value of the stomach level measurement between the threshold stomach level and the stomach fullness level.

In certain aspects of the present invention, nutritional training also includes the ongoing or occasional monitoring of the stomach fullness volume after the threshold value is initially set. As the baby grows, the stomach often increases in maximum capacity. If the stomach fullness volume increases, the threshold value may be recalculated and increased so as to continue to correspond to a relatively full stomach. Alternatively, the threshold value may be automatically recalculated by a measurement device, such as a monitor, as described below.

In one aspect of the present invention, the objective measurement of a physiological trait or volume indicative of the physical state of the stomach may be a measurement of the stomach volume and/or level, either estimated, measured, or calculated via an algorithm. The objective measurement may be a measurement of a linear, perimetric, circumferential, or volumetric dimension of the stomach, a cross-sectional area of the stomach, and/or of the stomach shape. The objective measurement may also be a measurement of a linear, perimetric, circumferential, surface area, or volumetric dimension of the torso, a cross-sectional area of the torso, and/or of the torso shape. Likewise, the objective measurement may be a measurement indicating the presence of the stomach in a specific region of the torso, because the stomach might move as it fills and expands. Similarly, the distention of the stomach, the tension in the stomach walls, the electrical activity in the muscles or nerves surrounding the stomach, the optical properties of the stomach, the acoustic properties of the stomach, the compression of the tissues surrounding the stomach, or the distention of the skin in the region of the torso containing the stomach, or any other measurable physical change or physiological trait or volume in the baby's anatomy that is related to or correlatable with an increase in breast milk volume in the baby's stomach, may be objectively measured to ascertain the state of fullness of the stomach. In general, the objective measurement may be any measurement that can be correlated to one or more of the aforementioned parameters that are indicative of the state of fullness of the stomach. The objective measurement of the state of fullness of the stomach may employ any suitable modality of automatic sensing, including ultrasound, audible sound, light (including coherent light), infrared radiation, and active or passive electrical properties, including EMG signals and electrical impedance measurements. The employed modality is preferably non-invasive.

In one aspect of the present invention, the measurement of the state of fullness of the stomach uses ultrasound to provide a measurement or empirical indication or estimate of the stomach dimensions, cross-sectional area, and/or volume of the stomach. In certain aspects of the present invention, ultrasound is used to measure the distention of, or tension in, the walls of the stomach, the blood flow in the stomach walls, vibration in the stomach walls, or the acoustic transmission properties of the tissues surrounding the stomach, which are affected by the relative compression of the tissues that are displaced as the stomach distends during filling.

Measurements indicative of the state of fullness of the stomach are performed by a stomach volume/level monitor or "stomach monitor." The stomach monitor may be used to determine both the stomach level and the stomach fullness volume, as well as any other stomach measurements. In one aspect of the present invention, a stomach monitor using ultrasound may generally include one or more ultrasonic transducers adapted to send pulsed ultrasonic energy into the baby's torso and to receive reflections of this energy. The stomach monitor may also include software to generate a measurement of the stomach state on the basis of the reflected ultrasonic energy and to compare it to a threshold value. The stomach monitor also may include one or more mechanisms to provide a signal or an alarm to the mother when the stomach signal reaches the threshold value. The signal or alarm may be provided in any suitable and useful form, such as an audible alarm, a tactile alarm, and/or a visible alarm.

In another aspect of the present invention, a stomach monitor measuring torso/skin distension may generally include one or more strain gauges adapted to measure the expansion of the skin of the torso due to the filling of the stomach within.

The stomach monitor may also include software to generate a measurement of the stomach state on the basis of the measured skin strain and to compare it to a threshold value. The stomach monitor also may include one or more mechanisms to provide a signal or an alarm to the mother when the stomach signal reaches the threshold value. The signal or alarm may be provided in any suitable and useful form, such as an audible alarm, a tactile alarm, and/or a visible alarm.

In still another aspect of the present invention, a stomach monitor may measure torso/skin durometer to determine the change in hardness or tautness of the skin of the torso due to the filling of the stomach within. The stomach monitor may also include software to generate a measurement of the stomach state on the basis of the measured skin durometer and to compare it to a threshold value. The stomach monitor also may include one or more mechanisms to provide a signal or an alarm to the mother when the stomach signal reaches the threshold value. The signal or alarm may be provided in any suitable and useful form, such as an audible alarm, a tactile alarm, and/or a visible alarm.

In another aspect of the present invention, the objective measurement of a physiological trait or volume indicative of the physical state of the stomach may be a measurement of breast volume and/or level, either estimated, measured, or calculated via an algorithm. The objective measurement may be a measurement of a linear, perimetric, circumferential, or volumetric dimension of the breast, a cross-sectional area of the breast, and/or of the breast shape. Similarly, the distention of the breast, the tension in the breast structures, the electrical activity in the muscles or nerves surrounding the breast, the optical properties of the breast, the acoustic properties of the breast, the compression of the tissues surrounding the breast, or the distention of the skin in the region of the torso containing the breast, or any other measurable physical change or physiological trait or volume in the mother's anatomy that is related to or correlatable with a reduction in breast milk volume in the mother's breast and therefore an increase in breast milk volume in the baby's stomach, may be objectively measured to ascertain the state of fullness of the stomach. In general, the objective measurement may be any measurement that can be correlated to one or more of the aforementioned parameters that are indicative of the state of fullness of the stomach. The objective measurement of the state of fullness of the breast may employ any suitable modality of automatic sensing, including ultrasound, audible sound, light (including coherent light), infrared radiation, and active or passive electrical properties, including EMG signals and electrical impedance measurements. The employed modality is preferably non-invasive.

In one aspect of the present invention, the measurement of the state of fullness of the breast uses ultrasound to provide a measurement or empirical indication or estimate of the breast dimensions, cross-sectional area, and/or volume of the breast. In certain aspects of the present invention, ultrasound is used to measure the distention of, or tension in, the walls and/or structures of the breast, the blood flow in and/or to the breast, vibration in the breast, or the acoustic transmission properties of the tissues surrounding the breast, which may be affected by the relative decompression of tissue as the breast reduces during emptying.

Measurements indicative of the state of fullness of the breast are performed by a breast volume/level monitor or "breast monitor." The breast monitor may be used to determine the breast level, as well as any other breast measurements. In one aspect of the present invention, a breast monitor using ultrasound may generally include one or more ultrasonic transducers adapted to send pulsed ultrasonic energy into the mother's breast and/or torso and to receive reflections of this energy. The breast monitor may also include software to generate a measurement of the breast state on the basis of the reflected ultrasonic energy and to compare it to a threshold value. The breast monitor also may include one or more mechanisms to provide a signal or an alarm to the mother when the breast signal reaches the threshold value. The signal or alarm may be provided in any suitable and useful form, such as an audible alarm, a tactile alarm, and/or a visible alarm.

In another aspect of the present invention, a breast monitor measuring torso/skin distension may generally include one or more strain gauges adapted to measure the contraction of the skin of the breast and/or torso due to the emptying of the breast. The breast monitor may also include software to generate a measurement of the breast state on the basis of the measured skin strain and to compare it to a threshold value. The breast monitor also may include one or more mechanisms to provide a signal or an alarm to the mother when the breast signal reaches the threshold value. The signal or alarm may be provided in any suitable and useful form, such as an audible alarm, a tactile alarm, and/or a visible alarm.

In still another aspect of the present invention, a breast monitor may measure torso/skin durometer to determine the change in hardness or tautness of the skin of the breast and/or torso due to the emptying of the breast. The breast monitor may also include software to generate a measurement of the breast state on the basis of the measured skin durometer and to compare it to a threshold value. The breast monitor also may include one or more mechanisms to provide a signal or an alarm to the mother when the breast signal reaches the threshold value. The signal or alarm may be provided in any suitable and useful form, such as an audible alarm, a tactile alarm, and/or a visible alarm.

In still another aspect of the present invention, the objective measurement of a physiological trait or volume indicative of the physical state of the stomach may be a measurement of the baby's physiological trait of swallowing, either estimated, measured, or calculated via an algorithm. The objective measurement may be a measurement of the number of times a baby swallows during a given breastfeeding session. The objective measurement of the state of fullness of the stomach may employ any suitable modality of automatic sensing, including ultrasound, audible sound, light (including coherent light), infrared radiation, and active or passive electrical properties, including EMG signals and electrical impedance measurements. The employed modality is preferably non-invasive.

In one aspect of the present invention, the objective measurement of swallowing indicative of the state of fullness of the stomach are performed by a "swallowing monitor." The swallowing monitor may use a microphone to acoustically detect the sounds emitted by the baby as it breast feeds. Such sounds, even if largely inaudible, may also be detected as sound conducted through bone or tissue. The sounds are then analyzed to determine the number of swallows indicative of stomach fullness. The stomach monitor may be used to determine both the stomach level and the stomach fullness volume by correlating the number of swallows with stomach fullness, as well as any other stomach measurements. In one aspect of the present invention, a swallowing monitor may generally include one or more microphones and signal processing hardware and software. The swallowing monitor may also include software to generate a measurement of the stomach state on the basis of the number of swallows and to compare it to a threshold value. The swallowing monitor also may include one or more mechanisms to provide a signal or an alarm to the mother when the stomach signal reaches the threshold value. The signal or alarm may be provided in any suitable and useful form, such as an audible alarm, a tactile alarm, and/or a visible alarm.

In addition to a microphone, it should be understood that any suitable sensor capable of sensing swallows may be used. For example, in an alternative embodiment, the baby's swallows can be monitored and counted by sensing muscular impulses occurring along the esophagus of the baby. In particular, during swallowing, the muscles surrounding the esophagus undergo a peristaltic action. Electrical impulses are generated in the nervous system that in turn fires the muscles that cause swallowing to occur. In one embodiment, for instance, the electrical impulses can be monitored using electromyography (EMG).

Electromyography is a medical technique for evaluating and recording physiological properties of muscles at rest and while contracting. Electromyography is performed using an instrument called an electromyograph to produce a record called an electromyogram. An electromyograph detects the electrical potential generated by a muscle or a group of muscles when the muscles contract, and also when the muscles are at rest. For instance, the muscle membrane potential is about −70 mV. During electromyography, measured potentials can range between less than 50 uV to greater than 30 mV. Typical repetition rate of muscle unit firing is from about 7 Hertz to about 20 Hertz, depending upon the size of the muscle. In the past, electromyography was used to assess muscle damage. Electromyography, however, is well suited to monitoring and counting swallows as they occur.

In general, there are two types of electromyographs. The first type is an intramuscular electromyograph, while the second type is called a surface electromyograph. Intramuscular electromyography typically involves inserting a needle electrode through the skin into the muscle in order to measure electrical activity.

Perhaps better suited for use in the process of the present disclosure, however, is surface electromyography. During surface electromyography, electrodes are placed on the skin overlying the muscle to detect the electrical activity of the muscle. In the present case, for instance, one or more sensors may be placed along the esophagus of the baby. The electrode sensor, for instance, may be elongated with several measurement points to record and observe the muscle contractions along the esophagus as the peristaltic action occurs during swallowing. For example, in one particular embodiment, the electrode placed upon the skin of the baby may comprise a textile material screen printed with silver.

One particular embodiment of using surface electromyography to detect swallowing is disclosed, for instance, in U.S. Pat. No. 6,484,053, which is incorporated herein by reference. In the '053 patent, for instance, surface electromyography is proposed for treating poor laryngeal-elevation disorder. In the '053 patent, the surface electromyograph includes cup-shaped surface electrodes made of gold plated silver that are configured to be placed over the submandibular salivary glands in order to send signals from the glossal muscle or from the temporalis muscle. The surface electrodes are connected to a signal processing circuit that, for instance, may amplify signals received from the electrodes for analyzing the signals using various software.

According to the present disclosure, electromyography may be used to sense muscular impulses around the esophagus. The muscle impulses can be measured for quantity of swallows, intensity of impulses and duration if desired. These factors may be used to calculate a volume of nutritional composition, such as breast milk, consumed by the baby.

Figure 2:
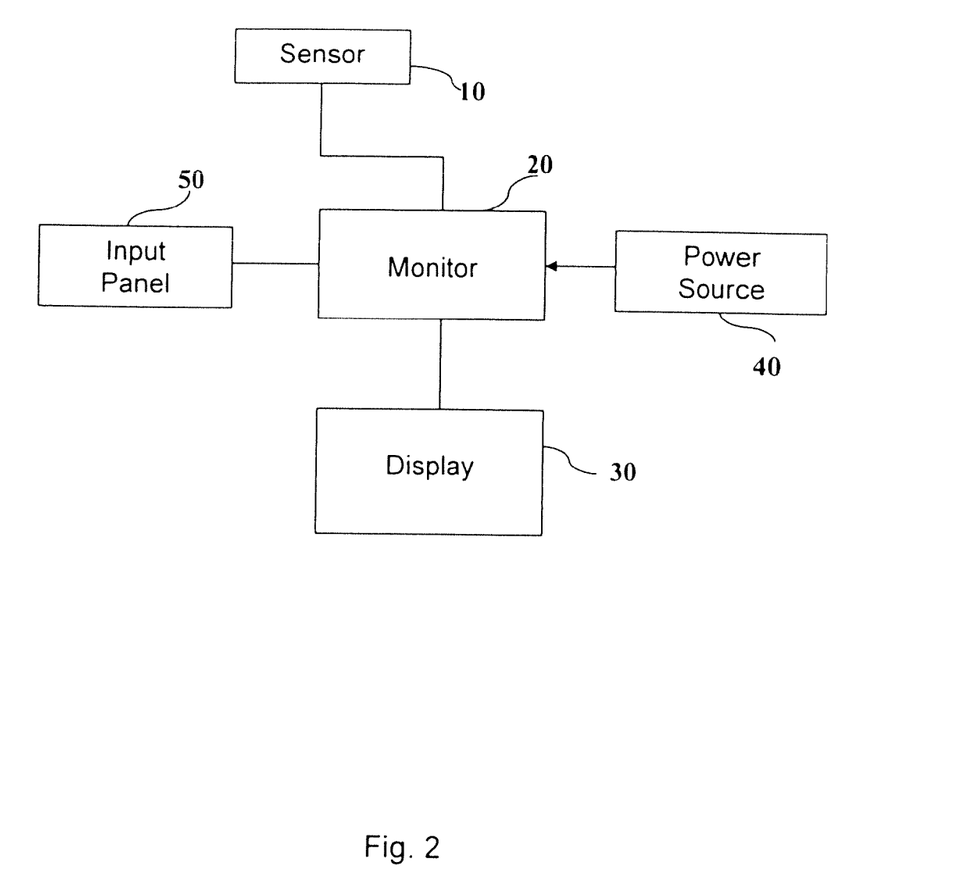
FIG. 2 is a diagram of one embodiment of a system made in accordance with the present disclosure.

One embodiment of a system for sensing swallows and determining the volume of liquid consumed by the baby is shown, for instance, in FIG. 2. As illustrated, the system includes a sensor 10 which may include, for instance, an electromyograph such as a surface electromyograph. The sensor 10 is in communication with a monitor 20. The monitor 20 can be any suitable programmable device, such as a microprocessor. The monitor, for instance, can be configured to receive information from the sensor to determine the number of swallows that have occurred by the baby and any other information that the sensor is capable of recording and transmitting to the monitor. The monitor 20 can then include an algorithm capable of calculating the amount of volume of nourishing composition swallowed by the baby based upon the information received from the sensor 10.

As shown in FIG. 2, the monitor 20 can include a display 30 for communicating information to the user regarding the volume of nourishing composition consumed by the baby. The monitor 20, for instance, can use the display 30 for communicating various information to the user. For instance, in addition to calculating the volume of breast milk consumed by the baby, the display may also be configured to calculate and determine the stomach level and the stomach fullness volume based upon the volume of composition consumed. As described above, the monitor may include one or more mechanisms to provide a signal or an alarm to the mother when the stomach fullness volume or the volume consumed by the baby reaches a threshold value.

As shown in FIG. 2, the monitor 20 can be connected to any suitable power source 40. The power source 40 can comprise, for instance, a battery or can comprise an AC outlet.

In one particular embodiment, the system can further include an input panel 50. The input panel 50 may be used to input into the system information about the baby that may be relevant or otherwise used to assist in calculating the volume of composition being consumed by the baby. For instance, a user may input into the input panel 50 the sex of the baby, the age of the baby, the height and weight of the baby, and the like. This information may be used to calculate an average volume of composition consumed during each swallow or may be used to calculate a stomach volume.

In another alternative embodiment of the present disclosure, swallowing may be monitored using acoustic myography (AMG). Acoustic myography is the recording of sounds produced by contracting muscles. These sounds generally become louder with increasing force of contraction. Analysis of acoustic signals from muscles can provide another noninvasive method for monitoring and recording swallows.

For example, during contraction, muscles generate sounds that under ordinary conditions are typically not heard. The sounds typically have a frequency of about 25 Hertz. Using a proper sensor, however, these sounds can be monitored and sensed.

When placed along the esophagus of a baby, the acoustic signals generated by the throat muscles during swallowing can be detected and used to monitor swallowing by the baby. One embodiment of a process for monitoring muscles through acoustic myography is disclosed, for instance, in U.S. Pat. No. 4,571,750, which is incorporated herein by reference.

The acoustic myograph, for instance, may include a sensor comprising a microphone connected to a preamplifier. The preamplifier may be connected to a rectifier which produces a DC signal. The rectifier in turn may be coupled to a differential amplifier which produces a signal that is fed to a bandpass filter which, in one embodiment, may be tuned into the vicinity of 20 Hertz to 30 Hertz. The filtered output signal can then be analyzed to record when a swallow has occurred and, in some embodiments, also record other information about the swallow, such as intensity and duration which may be used to calculate volume of liquid consumed during the swallow.

In addition to electromyography and acoustic myography, in still another embodiment, swallowing can be recorded by sensing movements in the throat using other types of sensors. For instance, in one embodiment, a bendable material may be used as a sensor that changes characteristics as it is stretched or manipulated. The bendable material, for instance, may be placed over the esophagus of a baby for recording swallows as they occur.

In one aspect of the present invention, any of the monitors described herein include a mechanism to calibrate the monitor and/or to reset the signal threshold value, and the electronics and power source to support the system. The monitor may be calibrated and the signal threshold value may be reset automatically or upon the intervention of the mother. Similarly, the type and intensity of the alarm may preferably be changed by the mother. Optional components of a monitor include a display, a data storage and analysis mechanism, a telemetry system, a remote mother alarm unit, and one or more mechanisms to secure the monitor to the baby or to a supporting garment. For example, the monitor may have the capability to store data that are useful for the tracking and assessment of progress toward the achievement of suitable nutrition. Ongoing collected data may be used to fine tune threshold volume levels and monitor trends.

The monitor used in the method of the present invention may be or include a handheld unit or may include a wearable device. As used herein, the term "wearable" refers to the adaptability of the monitor, or a portion thereof, to be applied to a baby's or mother's body for the duration of his or her normal activities without substantially limiting these activities. The scope of this term includes the association with, or incorporation into, a garment, the partial or full encirclement of at least a portion of the subject's anatomy, the adhesive application to the baby's or mother's skin, or the design of the device to simulate a garment, belt, or any other wearable garment. Wearable devices or components may include elastic and other belts, disposable or durable clothing, disposable absorbent articles such as diapers, disposable waste-receiving articles such as adhesively or releasably attachable strips such as bandages and diagnostic strips, adhesively-attached devices, and any other suitable wearable items. Additionally, the device, or a component of the device, may be releasably affixed to any of the above wearable articles or to any other carrier structure that may be attached to the subject or to a wearable article.

For example, the monitor may include an ultrasonic transducer or microphone affixed adhesively to the subject's skin or a strain gauge embedded in the baby's or mother's clothing and connected by wire or wirelessly to a closed housing containing the monitor electronics and power supply, which may be affixed to one of the subject's garments. Alternatively, the monitor may include an ultrasonic transducer, microphone, or a strain gauge integrated into a housing and the housing may be formed as, or incorporated into, a belt that may be applied around all or part of the subject's body. In the aspect of measuring a baby's stomach, the ultrasonic transducer or strain gauge should be held in intimate contact with the subject's skin in the vicinity of the torso above the navel.

Suitable ultrasonic devices and approaches to obtain objective measurements of the physical state of internal organs are described in U.S. Pat. Nos. 4,926,871; 5,322,067; 6,110,111; and 6,359,190; and U.S. Patent Application Publication No. 20050251036A1. Suitable strain gauge devices and approaches to obtain objective measurements are described in U.S. Pat. No. 5,454,376.

The nutritional training method of the present invention is significantly different from methods directed to observing internal organs, in that the present method is directed to training mothers to recognize a baby's traits indicative of stomach fullness. The monitor used in this method provides an indication that a baby has achieved stomach fullness and that an appropriate nutritional training opportunity exists. The accurate identification of appropriate nutritional training opportunities in the present method significantly increases the confidence and assurance of the mother with respect to her baby receiving suitable nutrition. Thus, the present method also reduces the psychological stress associated with breast-feeding a baby who cannot verbally communicate.

Measurements of the physiological trait or volume may be performed continuously or intermittently. Intermittent measurements may be performed automatically, at some preset or programmable interval driven by the monitor electronics, or manually by the mother. Preferably, measurements are made automatically at intervals of between about 5 seconds and about 10 minutes. More typically, the measurements are automatically made at intervals of between about 2 minutes and about 8 minutes. In another aspect of the present invention, measurements may be done continuously during breastfeeding.

In one aspect of the present invention, the monitor may be sold in a package including a monitor and instructions for using the monitor to perform the methods described herein. The term "instructions" referred to herein is an outline or manual of technical procedure for the use of the monitor. In general, the instructions may describe the use of the monitor for any of the steps for which it can be used. For example, the instructions may describe any of the steps mentioned, including those of using the monitor to obtain a stomach fullness volume and/or the objective measurement of a physiological trait or volume and providing an indication to the mother when the objective measurement equals or exceeds a signal threshold value. The instructions may also outline the potential actions, reactions, and/or demeanor to be exhibited by a baby with a full stomach as a part of identifying an appropriate nutritional training opportunity based on the occurrence of the signal. The instructions may, likewise, describe other steps, including those of using the monitor to measure the stomach fullness volume and setting the signal threshold value to correspond to a stomach volume that is less than the stomach fullness volume, for example.

The descriptive nature of the instructions may be provided by text, by figures or diagrams, or by any other visual guide, such as by the sequential numbering of operations or of operable devices in correspondence with an effective sequence of steps of the method of the present invention. Also, the instructions may be included with the package in any of several forms. For example, the instructions may be printed on the outside or the inside of the package itself, or may be in the form of a sheet or card contained inside the package or attached to the package. In some aspects of the present invention, the instructions may form part of the physical embodiment of the monitor as, for instance, when the instructions are engraved on, or affixed to, the monitor. In another aspect of the present invention, the monitor may include a display that displays, among other items, instructions for use of the monitor. In still another aspect of the present invention, the monitor may include audio instructions in its use. In general, the instructions may be provided in any form in which the functional relationship between the instructions and the use of the monitor is clear to the user.

These and other modifications and variations to the present invention may be practiced by those of ordinary skill in the art, without departing from the spirit and scope of the present invention, which is more particularly set forth in the appended claims. In addition, it should be understood that aspects of the various aspects of the present invention may be interchanged either in whole or in part. Furthermore, those of ordinary skill in the art will appreciate that the foregoing description is by way of example only, and is not intended to limit the invention so further described in such appended claims.

What is claimed:

1. A method for quantifying the amount of a nourishing composition that is being consumed by a baby comprising:
    sensing a baby's swallows during consumption of a nourishing composition using a non-invasive modality;
    determining a volume of the nourishing composition that is being consumed by the baby based on the number of swallows sensed;
    establishing a stomach fullness volume which corresponds to an average of the daytime breastfeeding volume;
    establishing a threshold value that corresponds to a stomach level that is proportional to the stomach fullness volume, the stomach level being based upon an amount of nourishing composition contained in the baby's stomach and being less than the stomach fullness volume;
    issuing an alert when the threshold value is reached; and
    recalculating the threshold value to correspond to increases in stomach fullness volume as the baby grows and the maximum capacity of its stomach increases.

2. A method as defined in claim 1, wherein the nourishing composition comprises breast milk.

3. A method as defined in claim 2, wherein the method is performed during breastfeeding between a mother and a baby.

4. A method as defined in claim 1, further comprising providing instructions to the caregiver to discontinue feeding of the baby.

5. A method as defined in claim 1, wherein the amount of sensed swallows by the baby are sent to a monitor that includes an algorithm to convert the number of sensed swallows into volume consumed by the baby.

6. A method as defined in claim 1, wherein the baby's swallows are sensed by a microphone.

7. A method as defined in claim 1, wherein the baby's swallows are sensed by sensing muscular impulses in an esophagus of the baby as the baby is swallowing.

8. A method as defined in claim 1, where the baby's swallows are sensed using electromyography.

9. A method as defined in claim 1, where the baby's swallows are sensed using surface electromyography.

10. A method as defined in claim 1, where the baby's swallows are sensed using acoustic myography.

11. A method as defined in claim 1, where the baby's swallows are sensed using a strain gauge.

12. A system for quantifying the amount of a nourishing composition that is being consumed by a baby comprising:
    a sensor that senses a baby's swallows using a non-invasive modality; and
    a monitor in communication with the sensor, the monitor being configured to determine a volume of the nourishing composition that is being consumed by the baby based on information received from the sensor;
    the monitor establishing a stomach fullness volume which corresponds to an average of the daytime breastfeeding volume;
    the monitor establishing a threshold value that corresponds to a stomach level that is proportional to the stomach fullness volume, the stomach level being based upon an amount of nourishing composition contained in the baby's stomach and being less than the stomach fullness volume;
    the monitor issuing an alert when the threshold value is reached; and
    the monitor recalculating the threshold value to correspond to increases in stomach fullness volume as the baby grows and the maximum capacity of its stomach increases.

13. A system as defined in claim 12, wherein the monitor includes a display for communicating volume information to user.

14. A system as defined in claim 12, wherein the monitor includes an algorithm that calculates the volume of the nourishing composition consumed by the baby based upon the number of swallows sensed by the sensor.

15. A system as defined in claim 12, wherein the sensor comprises a microphone.

16. A system as defined in claim 12, wherein the sensor comprises an electromyograph.

17. A system as defined in claim 12, wherein the sensor comprises a surface electromyograph.

18. A system as defined in claim 12, wherein the sensor comprises an acoustic myograph.

19. A system as defined in claim 12, wherein the sensor comprises a strain gauge.

20. A method as defined in claim 1 wherein the signal threshold value is set to correspond to a stomach fullness volume of 90% or less.

21. A method as defined in claim 1 wherein the signal threshold value is set to correspond to a stomach fullness volume of 80% or less.

22. A method as defined in claim 1 wherein the signal threshold value is set to correspond to a stomach fullness volume of 70% or less.

* * * * *